United States Patent
Hu et al.

(10) Patent No.: US 11,480,051 B2
(45) Date of Patent: Oct. 25, 2022

(54) APPLY MULTI-PHYSICS PRINCIPLE FOR WELL INTEGRITY EVALUATION IN A MULTI-STRING CONFIGURATION

(71) Applicant: Halliburton Energy Services, Inc., Houston, TX (US)

(72) Inventors: Yike Hu, Phoenix, AZ (US); Weijun Guo, Houston, TX (US); Burkay Donderici, Pittsford, NY (US)

(73) Assignee: Halliburton Energy Services, Inc., Houston, TX (US)

( * ) Notice: Subject to any disclaimer, the term of this patent is extended or adjusted under 35 U.S.C. 154(b) by 212 days.

(21) Appl. No.: 16/464,217

(22) PCT Filed: May 15, 2018

(86) PCT No.: PCT/US2018/032739
§ 371 (c)(1),
(2) Date: May 24, 2019

(87) PCT Pub. No.: WO2018/236495
PCT Pub. Date: Dec. 27, 2018

(65) Prior Publication Data
US 2020/0109626 A1    Apr. 9, 2020

Related U.S. Application Data

(60) Provisional application No. 62/522,518, filed on Jun. 20, 2017.

(51) Int. Cl.
*E21B 47/13* (2012.01)
*G01V 3/18* (2006.01)
(Continued)

(52) U.S. Cl.
CPC ............ *E21B 47/13* (2020.05); *G01V 3/18* (2013.01); *G01V 3/38* (2013.01); *G01V 5/045* (2013.01);
(Continued)

(58) Field of Classification Search
CPC . E21B 47/13; G01V 3/18; G01V 3/38; G01V 5/045; G01V 5/12; G01V 5/14; G01V 11/002
(Continued)

(56) References Cited

U.S. PATENT DOCUMENTS 3,123,709 A * 3/1964 Caldwell ............... G01V 5/12
250/269.3
4,539,649 A * 9/1985 Michaelis ............ G01N 23/12
702/137
(Continued)

FOREIGN PATENT DOCUMENTS

EP         0443936 A1    8/1991
WO    2015050661 A1    4/2015
(Continued)

*Primary Examiner* — Michael P Nghiem
(74) *Attorney, Agent, or Firm* — John W. Wustenberg; Parker Justiss, P.C.

(57) ABSTRACT

The disclosure provides a well integrity monitoring tool for a wellbore, a method, using a nuclear tool and an EM tool, for well integrity monitoring of a wellbore having a multi-pipe configuration, and a well integrity monitoring system. In one example, the method includes: operating a nuclear tool in the wellbore to make a nuclear measurement at a depth of the wellbore, operating an EM tool in the wellbore to make an EM measurement at the depth of the wellbore, determining a plurality of piping properties of the multi-pipe configuration at the depth employing the EM measurement, determining, employing the piping properties, a processed nuclear measurement from the nuclear measurement, and employing the processed nuclear measurement to determine (Continued)

an integrity of a well material at the depth and within an annulus defined by the multi-pipe configuration.

25 Claims, 8 Drawing Sheets

(51) Int. Cl.
*G01V 3/38* (2006.01)
*G01V 5/04* (2006.01)
*G01V 5/12* (2006.01)
*G01V 5/14* (2006.01)
*G01V 11/00* (2006.01)

(52) U.S. Cl.
CPC ............... *G01V 5/12* (2013.01); *G01V 5/14* (2013.01); *G01V 11/002* (2013.01)

(58) Field of Classification Search
USPC .............................................. 702/6
See application file for complete search history.

(56) References Cited

U.S. PATENT DOCUMENTS

| 2013/0085675 | A1* | 4/2013 | Prakash | E21B 49/003 |
| | | | | 702/9 |
| 2013/0345983 | A1 | 12/2013 | Guo | |
| 2016/0273335 | A1 | 9/2016 | Quintero | |
| 2017/0191361 | A1* | 7/2017 | Khalaj Amineh | E21B 47/13 |
| 2017/0352168 | A1* | 12/2017 | Jamison | E21B 47/002 |

FOREIGN PATENT DOCUMENTS

| WO | 2017011078 A1 | 1/2017 |
| WO | 2018236495 A1 | 12/2018 |

* cited by examiner

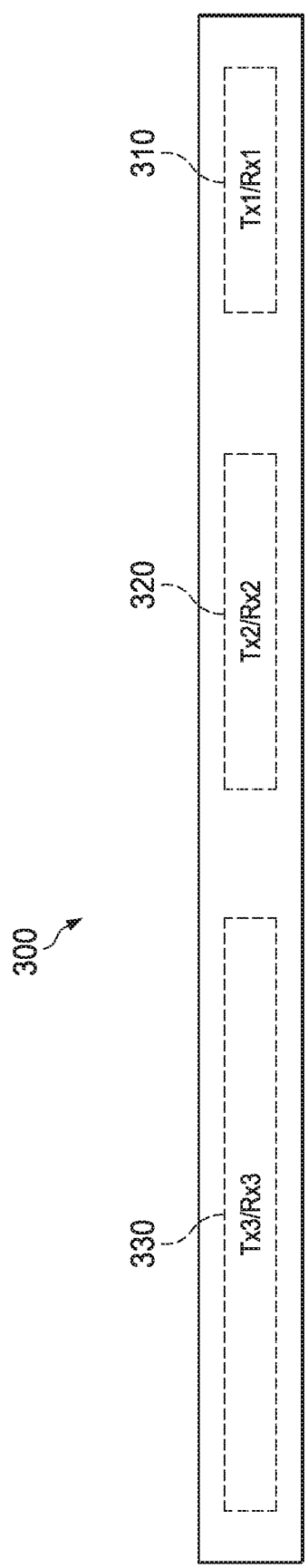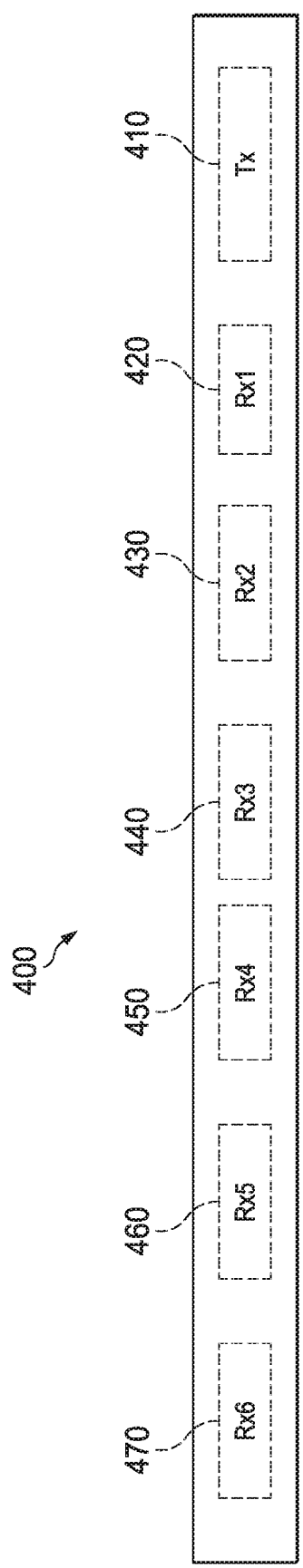

APPLY MULTI-PHYSICS PRINCIPLE FOR WELL INTEGRITY EVALUATION IN A MULTI-STRING CONFIGURATION

CROSS-REFERENCE TO RELATED APPLICATION

This application is the National Stage of, and therefore claims the benefit of, International Application No. PCT/US2018/032739 filed on May 15, 2018, entitled "APPLY MULTI-PHYSICS PRINCIPLE FOR WELL INTEGRITY EVALUATION IN A MULTI-STRING CONFIGURATION," which was published in English under International Publication Number WO 2018/236495 on Dec. 27, 2018, and claims benefit to U.S. Provisional Application No. 62/522,518 filed on Jun. 20, 2017. The above applications are commonly assigned with this National Stage application and are incorporated herein by reference in their entirety.

TECHNICAL FIELD

This application is directed, in general, to wellbores and, more specifically, to evaluating the integrity of a well material in a wellbore.

SUMMARY

In one aspect the disclosure provides a method, using a nuclear tool and an EM tool, for well integrity monitoring of a wellbore having a multi-pipe configuration. In one example, the method includes: operating a nuclear tool in the wellbore to make a nuclear measurement at a depth of the wellbore, operating an EM tool in the wellbore to make an EM measurement at the depth of the wellbore, determining a plurality of piping properties of the multi-pipe configuration at the depth employing the EM measurement, determining, employing the piping properties, a processed nuclear measurement from the nuclear measurement, and employing the processed nuclear measurement to determine an integrity of a well material at the depth and within an annulus defined by the multi-pipe configuration.

In another aspect the disclosure provides a well integrity monitoring tool for a wellbore. In one example, the well integrity monitoring tool includes: an EM tool configured to obtain EM measurements, at different depths of a wellbore, associated with metal pipes of a multi-pipe configuration of the wellbore, wherein the EM measurements correspond to piping properties of the metal pipes, and a nuclear tool configured to obtain nuclear measurements at the different depths of the wellbore, wherein the nuclear measurements correspond to volumetric information for a well material that is behind a multilayer of the metal pipes.

In yet another aspect, the disclosure provides a well integrity monitoring system. In one example, the well integrity monitoring system includes: a well integrity monitoring tool for a wellbore having an EM tool configured to obtain EM measurements at depths of a wellbore having a multi-pipe configuration, wherein the EM measurements correspond to piping properties of metal pipes of the multi-pipe configuration, and a nuclear tool configured to obtain nuclear measurements at the depths of the wellbore, and including an integrity computing device having an interface configured to receive the EM measurements and the nuclear measurements, and a processor configured to employ both the EM measurements and the nuclear measurements to determine an integrity of a well material at one of the depths and within an annulus defined by the multi-pipe configuration.

BACKGROUND

Hydrocarbons, such as oil and gas, are located in subterranean formations. To obtain the oil or gas, various well operations, such as drilling, logging, and completion, are performed. During these operations, casing is used to provide structural support, control pressures, and isolate water within a well. Tubing is typically used within the casing to retrieve the hydrocarbons from the subterranean formation and deliver the hydrocarbons to the surface of the well.

BRIEF DESCRIPTION

Reference is now made to the following descriptions taken in conjunction with the accompanying drawing, in which:

FIG. 3 illustrates a diagram of an example of a time-domain EM tool used for pipe inspection;

FIG. 4 illustrates a diagram of an example of a frequency-domain EM tool used for pipe inspection.

DETAILED DESCRIPTION

Figure 1:
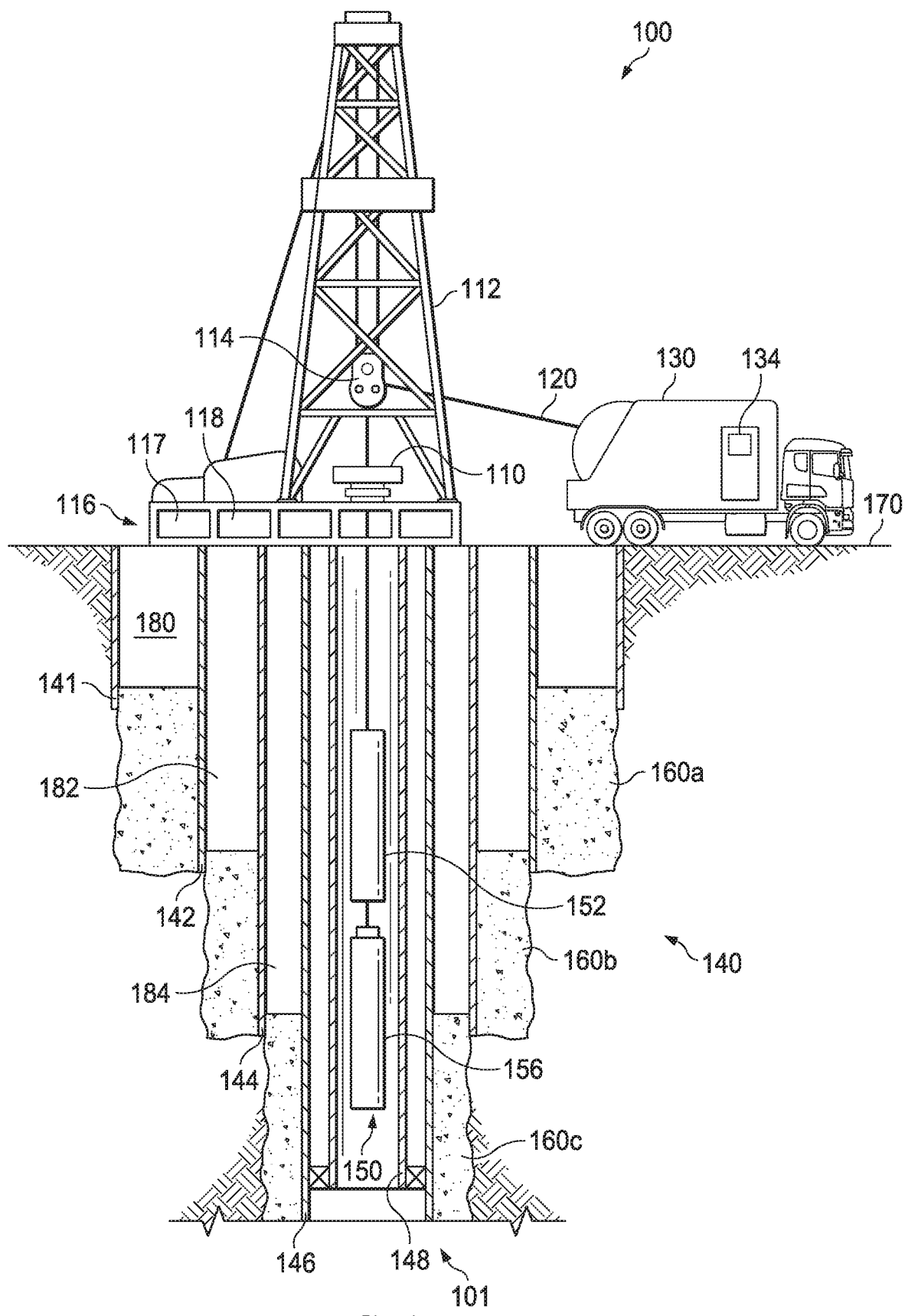
FIG. 1 illustrates a diagram of an elevation view in partial cross-section of a wellbore system configured to perform, for example, formation testing, sampling, or well integrity monitoring in a wellbore.

Cement is often used between multiple layers of casing, for structural support, pressure control, and fluid isolation. Throughout the various well operations, a well operator can place other materials besides cement, such as proppants and packing, within the well annuluses defined by the casings and tubing. During these well operations, and also when decommissioning a well, it is advantageous to know the volumetric information of cement or other well materials of interest located within the defined annuluses of the well.

The disclosure provides a well integrity monitoring tool, system, and method for determining the integrity of a well. The system, method, and tool employ a multiple physics approach to evaluate the integrity of a well material, such as cement, in a downhole multi-string configuration. A multi-string or multi-pipe configuration can include production tubing in place. The integrity or quality of the well material is volumetric information of the well material within an annulus or annuluses defined by multi-pipe configuration. The well material integrity can by the density of the well material within an annulus. A well material is a material added or injected to the well by, for example, the well operator. Well material includes cement (sometimes referred to as concrete), spacer, mud, proppant or other fluids or solid material injected into a wellbore during the various stages that include drilling, completion, production, and abandonment.

The multiple physics approach disclosed herein includes both nuclear and electromagnetic (EM) technology. For example, the disclosure provides a well integrity monitoring tool that includes both a nuclear tool, such as a nuclear cement evaluation tool (NCET), based on gamma-gamma scattering and an EM tool, such as an EM pipe inspection tool. Measurements obtained by the EM tool, i.e., EM measurements, provide thickness and spacing information about the metal casing and tubing, collectively referred to herein as metal piping. The EM measurements can provide, for example, five outputs or piping properties about the metal piping: tubing thickness, production casing thickness, distance between tubing and casing, distance between production casing and intermediate casing, and relative eccentricity between tubing and casing. Measurements obtained by the nuclear tool, i.e., nuclear measurements, provide density information about the well material located in the annuluses defined by the metal piping.

The well integrity monitoring tool can further include an integrity processor, implemented on a computer, that receives the EM and nuclear measurements from the EM tool and the nuclear tool and provide an accurate estimation of the volumetric information of well material behind metal pipes, for example, a multi-pipe configuration that has at least two layers of metal pipes that are steel pipes.

The disclosure, therefore, provides solutions for well integrity evaluation in a cased-hole environment. In particular, the disclosed tool, system, and method advantageously save time and costs associated with determining well integrity without removing tubing during various well procedures, such as, cement remedial procedure or cut and pull process at the well abandonment stage. The well integrity monitoring tool disclosed herein can be deployed through various conveyances, such as wireline, slickline or coiled tubing.

Turning now to the figures, FIG. 1 illustrates a diagram of an elevation view in partial cross-section of a wellbore system 100 configured to perform, for example, formation testing, sampling, or well integrity monitoring in a wellbore 101. The wellbore system 100 includes a wellhead 110, a derrick 112, and a traveling block 114 supported by the derrick 112. Wellbore system 100 may further include a controller 116 that directs operation thereof and includes a processor 117 and a memory 118. The wellbore system 100 further includes a conveyance 120 (such as wireline, slickline, coiled tubing, etc.), a logging facility 130, and a multi-pipe configuration 140. Wellbore system 100 can include a wireline tool, such as a probe or a sonde, that can be lowered to the bottom of a region of interest in the wellbore 101 and subsequently pulled upward at a substantially constant speed. The wireline tool in wellbore system 100 is a well integrity monitoring tool 150 as disclosed herein that forms part of a wireline logging operation. The conveyance 120 can be used to raise and lower the well integrity monitoring tool 150 into and out of the wellbore 101 to gather data for evaluation of the integrity of well material within the multi-pipe configuration 140. The data obtained by the well integrity monitoring tool 150 can be communicated to the surface logging facility 130 for storage, processing, and/or analysis. Logging facility 130 may be provided with electronic equipment 134, including processors for various types of signal processing and communication of information. One of the processors can be configured to perform the functions of the integrity computing device illustrated in FIG. 10. The controller 116 could also be used to perform at least some of the functions of the integrity computing device disclosed herein.

The multi-pipe configuration 140 includes multiple casing strings that are set inside the drilled wellbore 101 to protect and support production of hydrocarbons to the surface 170. In addition to providing stabilization and keeping the sides of the wellbore 101 from caving in on themselves, the casing strings can protect hydrocarbon production from outside contaminants, such as separating any fresh water reservoirs from fluids being produced through the casing. Also known as setting pipe, casing a wellbore 101 includes running pipe (such as steel pipe) down an inside of the recently drilled portion of the wellbore 101. The small space between the casing and the untreated sides of the wellbore 101 (generally referred to as an annulus) can be filled with a well material to permanently set the casing in place. The well material can be cement and will be referred to as cement in the following discussion of FIG. 1. Casing pipe can be run from a floor of the derrick 112, connected one joint at a time, and stabbed into a casing string that was previously inserted into the wellbore 101. The casing is landed when the weight of the casing string is transferred to casing hangers which are positioned proximate the top of the new casing, and can use slips or threads to suspend the new casing in the wellbore 101. A cement slurry can then be pumped into the wellbore 101 and allowed to harden to permanently fix the casing in place. After the cement has hardened, the bottom of the wellbore 101 can be drilled out, and the completion process continued.

Sometimes the wellbore 101 is drilled in stages. For example, wellbore 101 can be drilled to a certain depth, cased and cemented, and then the wellbore 101 is drilled to a deeper depth, cased and cemented again, and so on. Each time the wellbore 101 is cased a smaller diameter casing is used. The multi-pipe configuration 140 includes a conductor pipe 141, surface casing 142, intermediate casing 144, production casing 146, and production tubing 148. The conductor pipe 141 is the widest type of casing, and is usually about 30 to 42 inches in diameter for offshore wellbores and 12 to 16 inches in diameter for onshore wellbores. An annular space (not shown in FIG. 1) radially outside the conductor pipe 141 can be filled with cement to prevent drilling fluids from circulating outside the conductor pipe and causing erosion. The surface casing 142 is the next size in casing strings and can run several thousand feet in length. An annular space 180 radially outside the surface casing 142 can be filled with cement 160a to prevent, for example, hydrocarbon fluids from encroaching into fresh water zones. The intermediate casing 144 is next is diameter size and can be run to separate challenging areas or problem zones, such as areas of high pressure or lost circulation. An annular space 182 radially outside the intermediate casing 144 can be at least partially filled with cement 160b to, for example, isolate formations which can possibly breakdown and cause a loss of circulation in the wellbore.

Generally, the last type of casing string run into the wellbore 101 is the production casing 146, and is therefore the smallest diameter casing string. The production casing 146 can be run directly into a producing reservoir. An annular space 184 radially outside the production casing 146 can be at least partially filled with cement 160c to, for example, stop hydrocarbons from migrating to thief zones and to prevent sloughing of formations which can cause circulation loss in the wellbore 101. A production tubing 148 can then be run in the wellbore 101 to produce hydrocarbons from the producing reservoir to the surface 170 and the derrick 112. A liner string (not shown) can also be run into the wellbore 101. While similar to other casing strings, a liner string is not run the complete length of a wellbore but is hung by a liner hanger. As with the casing strings, the annular space radially outside a liner string can also be filled or at least partially filled with cement.

The well integrity monitoring tool 150 employs a multiple physics approach to evaluate the integrity of well material within the multi-pipe configuration 140. The well integrity monitoring tool 150 includes an EM tool 152 and a nuclear tool 156 that are shown conveyed in tandem inside the production casing 146 by the conveyance 120. The EM tool 152 and the nuclear tool 156 can be used to evaluate the integrity of the cement 160a-c behind casing when the well integrity monitoring tool 150 is operating inside the production tubing 148. The EM tool 152 and the nuclear tool 156 make EM measurements and nuclear measurements, respectively, at various depths in the wellbore 101. The corresponding EM and nuclear measurements can then be evaluated with respect to well material relationship maps to determine the integrity of the cement or volumetric information of other well material The EM tool 152 and the nuclear tool 156 may be separate tools which may be designed for the purposes described below, or they may be existing EM and nuclear tools which are normally operated individually for EM inspection and nuclear logging purposes. The order of the EM tool 152 and the nuclear tool 156 can vary in different applications. For example, the nuclear tool 156 can be above the EM tool 152 when conveyed. In one example, the EM tool 152 and the nuclear tool 156 are combined into one tool body by collocating various components of the tools to provide a single combined integrity monitoring tool. The nuclear tool 156 can be the nuclear tool 200 of FIG. 2A.

Figure 2B:
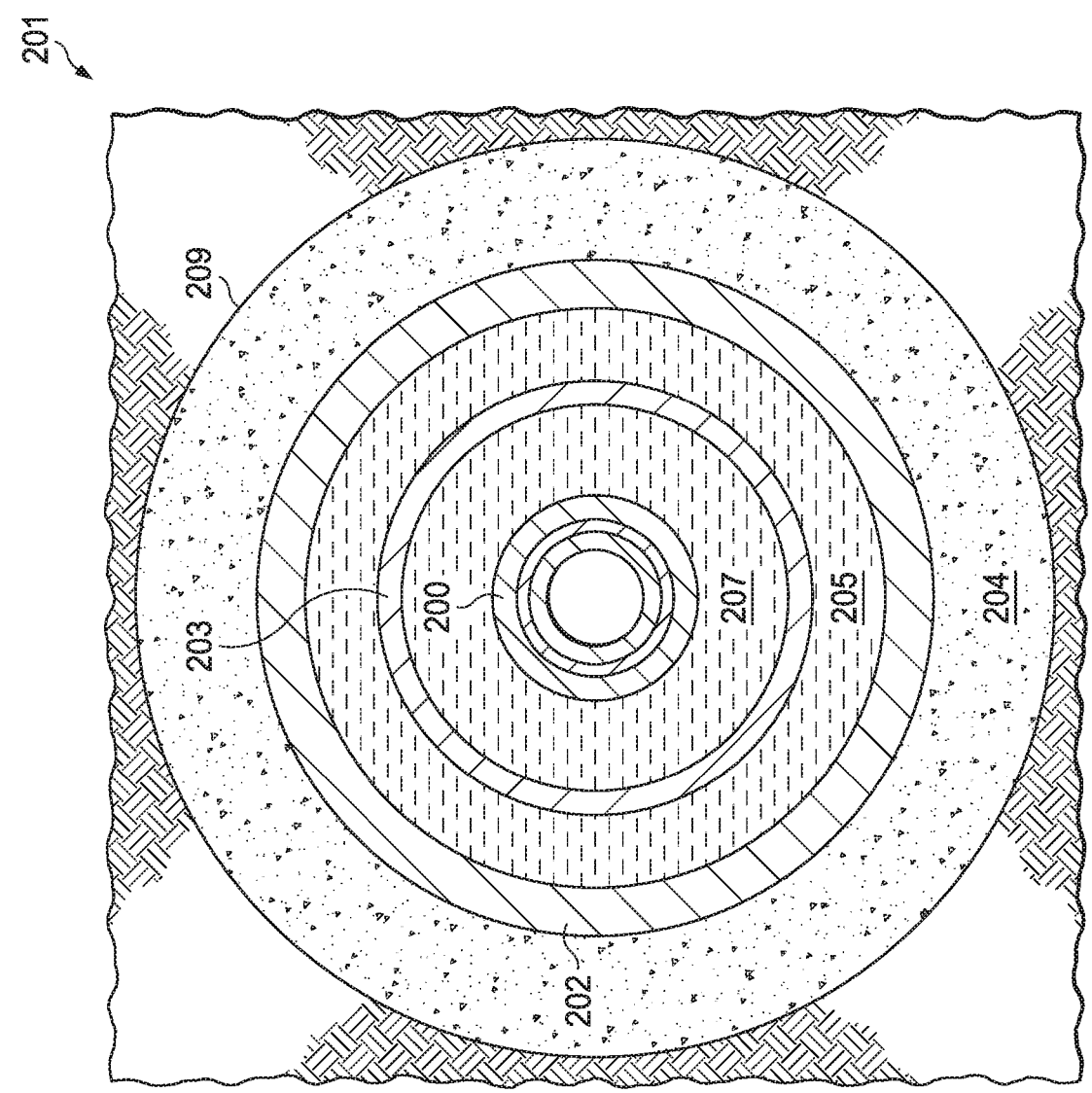
FIG. 2B illustrates a cross-section view of the nuclear tool of FIG. 2A in a wellbore having a multi-pipe configuration.
Figure 2A:
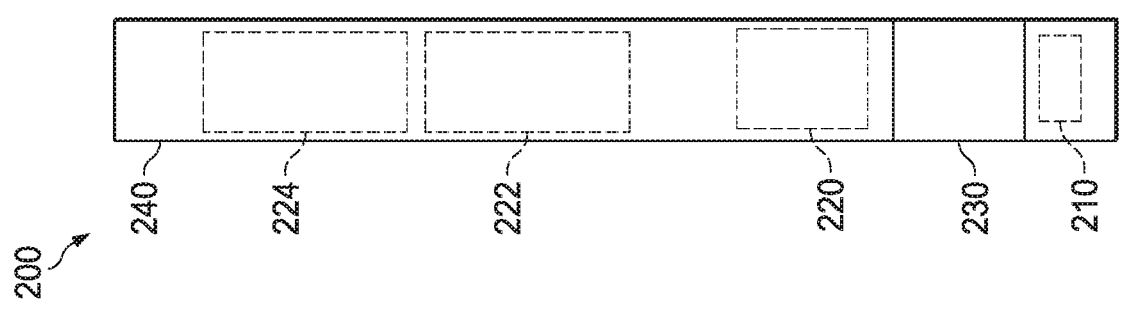
FIG. 2A illustrates a side view of an example nuclear tool.

FIG. 2A illustrates a side view of an example nuclear tool 200 and FIG. 2B illustrates a cross-section view of the nuclear tool 200 in a wellbore 201 having a multi-pipe configuration. The nuclear tool 200, such as a NCET, is based on the attenuation of gamma rays and includes an omnidirectional gamma source 210 that emits gamma rays toward the full circumference area of the wellbore 201.

In the illustrated example, the nuclear tool 200 is a three-detector configuration. The three detectors, first detector 220, second detector 222, and third detector 224, are placed at a pre-determined distance from the gamma source 210, and are collimated to detect gamma rays at a certain depth in the wellbore 201 that are scattered from the wellbore 201, the piping within the wellbore and well material behind the piping. The nuclear tool 210 includes a barrier 230 that is located between the gamma source 210 and the three detectors 220, 222, 224, to prevent the three detectors 220, 222, 224, from obtaining gamma rays scattered inside the tool body 240 directly from the gamma source 210. The barrier 230 is constructed of a heavy metal that heavily attenuates gamma rays. Each of the gamma ray detectors 220, 222, 224, obtains nuclear measurements by measuring the energy distribution of the number of photons deposited at the particular detector (count rates per second).

The nuclear tool 200 can include more or less than three gamma ray detectors. The greater number of gamma ray detectors that are located close to the gamma source 210 provide more details of the surrounding area proximate the nuclear tool 200. When there are more gamma ray detectors located distal from the gamma source 210, an increase in the details away from the nuclear tool 200 can be obtained.

The energy range applied with the nuclear tool 200 is generally below a few hundreds keV. For example, a source of Cs-137 has energy level of 662 keV. The elements encountered by the gamma rays in the downhole environment such as wellbore 201 have very similar attenuation coefficients, which in term stay relatively constant over the full energy range of interest. Therefore the total number of count rates measured is mainly determined by the density of materials that the gamma rays interact with along their path from the gamma source 210 to one of the gamma ray detectors 220, 222, 224. This is the nuclear measurement principle behind the gamma-gamma technique for the nuclear tool 200.

As illustrated in FIG. 2B, the gamma rays encounter layers of materials outside the nuclear tool 200 along their traveling path. The layers of material include the multi-pipe configuration and the well material within the annuluses defined by the multi-pipe configuration. The multi-pipe configuration includes production casing 202 and production tubing 203 and the layers of well material include cement 204 inside the primary cement sheath (behind the production casing 202 and within the inner diameter 209 of the wellbore 201), borehole fluid 205, and tubing fluid 207. In some applications, the well material, such as the borehole fluid 205 and the tubing fluid 207, are assumed to be known for the procedures related to a particular wellbore application.

FIG. 3 illustrates a diagram of an example of a time-domain EM tool 300 used for pipe inspection and FIG. 4 illustrates a diagram of an example of a frequency-domain EM tool 400 used for pipe inspection. The EM tool 152 of FIG. 1 can be either the EM tool 300 or the EM tool 400. Both the EM tool 300 and the EM tool 400 include transmitter and receiver coils that provide and receive electromagnetic energy, and can both be conventional tools. In the time-domain tool EM tool 300, pulses are used as the excitation and transmitters and receivers are collocated. EM tool 300 includes three collocated transmitters and receivers 310, 320, 330. Alternatively single coil transceivers can be used, where the same coil serves both as the transmitter and the receiver.

Frequency-domain tool EM tool 400 includes a transmitter 410 and six receivers denoted as receivers 420, 430, 440, 450, 460, and 470. EM tool 400 excitation has a limited spectral content centered around one or a small number of frequencies and a steady-state phasor-domain measurement is made. Typical frequencies for the frequency domain EM tool 400 may range from 0.1 Hz to 100 Hz. Low frequencies allow deeper penetration and are important to achieving sensitivity to second, third or deeper pipes. Higher frequencies allow measurement of a first pipe with less influence from the other pipes. Similarly, for the time domain tool EM tool 300, late time values are indicative of deeper pipe features or properties, while early time values are indicative of shallower pipe properties. By using well log signals at multiple frequencies (for frequency-domain EM tool 400) or multiple time points (for time-domain EM tool 300), it is possible to solve for both first and subsequent pipe properties. This can be accomplished using an inversion process where modeled signals are matched to the EM well log signals and the model parameters that correspond to the best match are accepted as the outputs. The EM well log signals are EM signals provided by or measured by an EM tool such as the EM tool 300 or EM tool 400.

Figure 5:
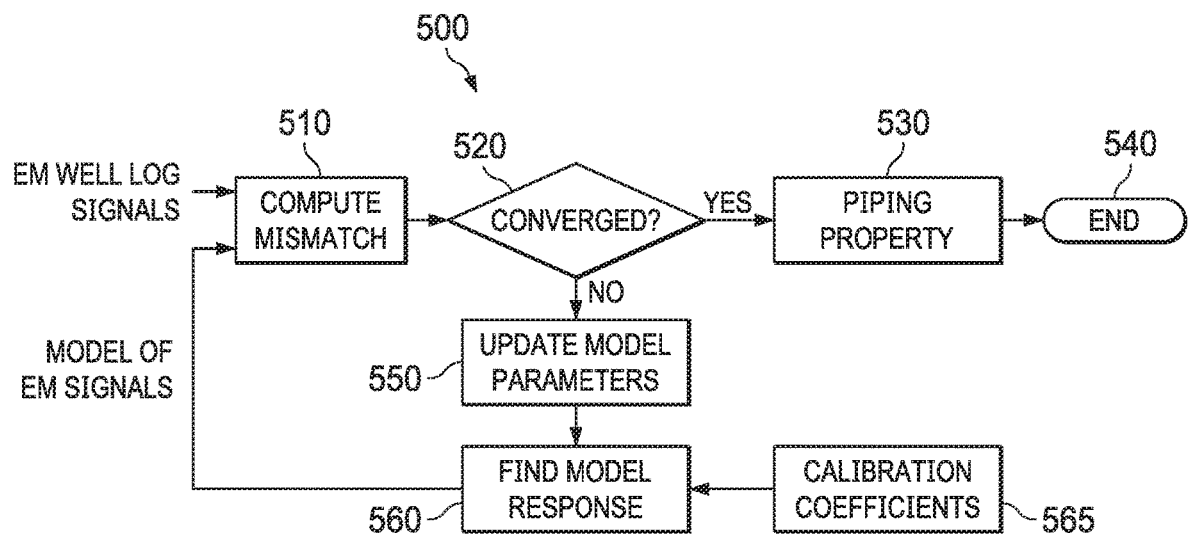
FIG. 5 illustrates a flow diagram of an example of a workflow of an inversion algorithm to determine piping properties, such as thickness of metal piping.

FIG. 5 illustrates a flow diagram of an example of a workflow 500 of an inversion algorithm to determine piping properties, such as thickness of metal piping. A series of operating instructions or code can direct the operation of a processor to perform the inversion algorithm represented by the workflow 500 to determine the pipe properties. The processor can be part of the electronic equipment 134. In some examples a computing device downhole can perform the method 500 and communicate the results to a computing device at the surface via standard communication methods employed in a wellbore. The method 500 generates an output indicating a piping property or properties of a multi-pipe configuration by comparing measured EM well log signals to signals from a model response, and tweaking the model until an expected modelling signal is obtained that corresponds to the measured EM signals from the well log, i.e., the EM well log signals.

The workflow 500 begins in a step 510 by computing a mismatch between EM well log signals and model signals. The EM well log signals can be measured EM signals from an EM tool, such as EM tool 300 or EM tool 400. The model signals are also EM signals generated according to a model response based on model parameters.

A determination is made in decision step 520 if the difference or mismatch between the EM well log signals and the model signals have converged. Convergence is typically determined by the number of iterations for an iterative algorithm, or amount of mismatch between the model signals and the well log signals. If convergence has occurred, a piping property or feature is provided in step 530. The workflow ends in a step 540. Multiple piping properties can be provided. The output of piping properties provided in step 530 can be, for example, the determined thicknesses of individual casings of a multi-pipe configuration. In various examples, the piping properties determined by the workflow 500 and the model that is used in the workflow 500 correspond to the multi-pipe configuration.

If convergence has not occurred, then the method 500 continues from step 520 to step 550 where the model parameters are updated. Model parameters can be: tubing thickness, production casing thickness, distance between tubing and casing, distance between production casing and intermediate casing, and relative eccentricity between tubing and casing. The parameters that are known before performing the workflow 500 can either be constrained during the inversion process, or they can be used as inputs to the workflow 500 rather than outputs. For example, if the diameter of a pipe is known based on a given well-plan, the diameter can be fixed to be that value in the inversion workflow 500. Alternatively the known pipe diameter can be allowed to change within a certain percentage of the known pipe diameter value (i.e., constraint). The model response is then generated with the updated model parameters in step 560. The model response can be generated using a conventional method. In a step 565, calibration coefficients are received for generating the model response. The calibration coefficients can be provided for the first generation of the model response based on historical data. For example, the calibration coefficients can be obtained from the tool response characterization in lab testing or computer simulation for the same type of tool.

Figure 6:
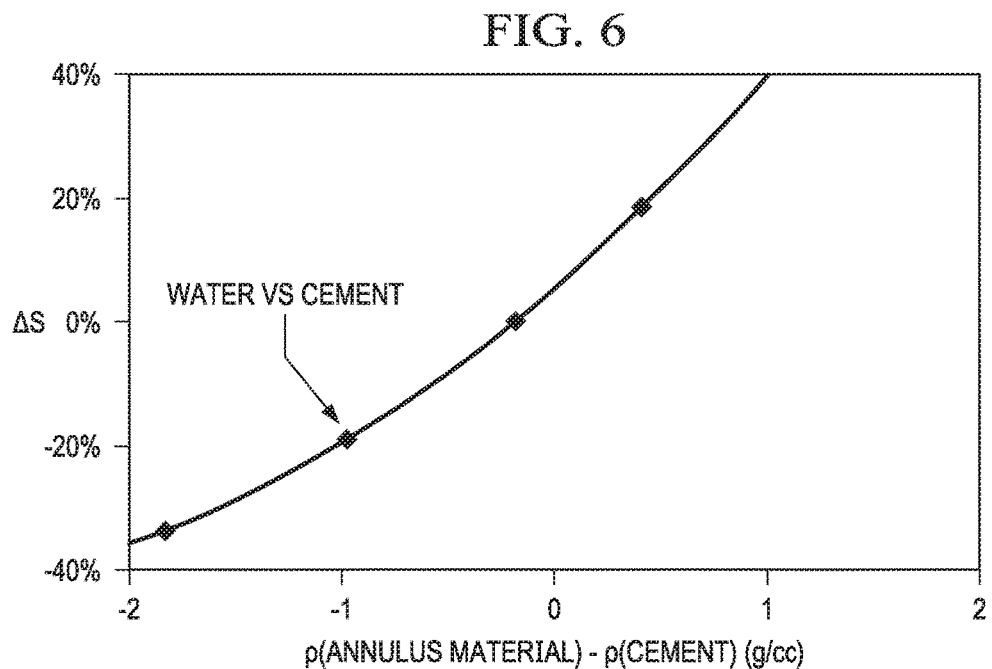
FIG. 6 illustrates an example of a well material relationship map corresponding to a signal change ($\Delta S$)
Figure 7:
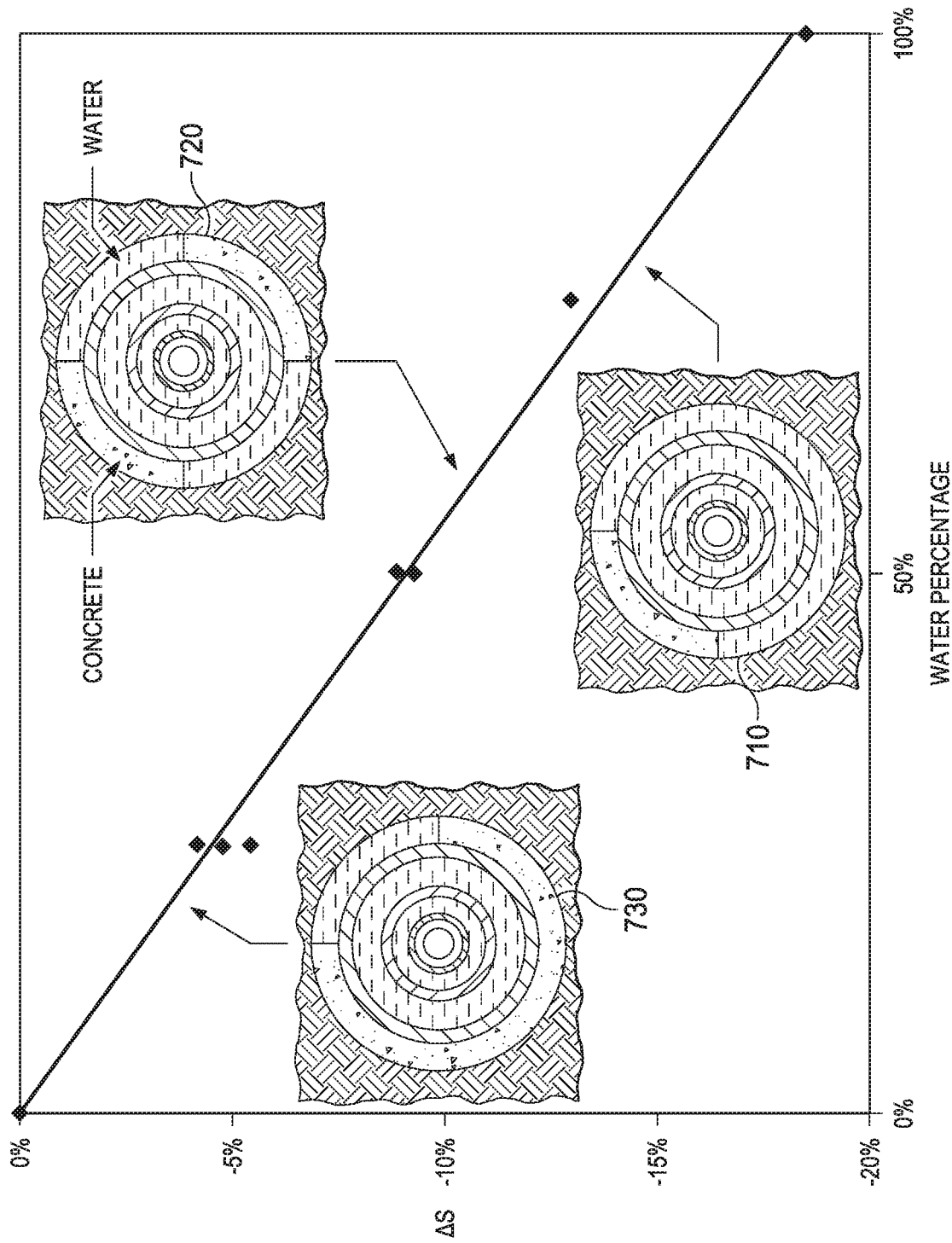
FIG. 7 illustrates another example of a well material relationship map that illustrates a nuclear tool signal contrast dependence on the volumetric fraction of cement inside a primary cement sheath.

As noted previously, the well integrity monitoring tool disclosed herein, such as tool 150, can be used to determine the volumetric information of well material injected into a wellbore. The piping properties determined via the EM measurements can be used with the nuclear measurements obtained by the detectors of a nuclear tool to determine the volumetric information. The piping properties, such as the measured casing thickness, are used to determine which well material relationship map or chart to use that represents the multi-pipe configuration in a wellbore. The illustrated charts of FIG. 6 and FIG. 7 provide examples of the relationship between the EM and nuclear measurements and the volumetric information of a well material in a wellbore. The chart of FIG. 6 can be established from experimental or modelled data. Different charts are used depending on the well material being investigated. Additionally, the metal piping thickness determined from the EM tool measurements as shown in FIG. 5 are used to determine the particular chart to use. Both FIG. 6 and FIG. 7 represent well material relationship for a particular casing thickness and well material. As with FIG. 6, the determined metal piping thickness and well material determine the particular well material relationship to use that corresponds to FIG. 7. As with FIG. 6, experimental and modelled data can also be used to generate the various well material relationship map such as illustrated in FIG. 7. Different relationship maps are established for different casing thicknesses and different well materials. Computer simulations can be used to develop the well material relationship maps. Signal processing using a combination of data acquired at each detector of a nuclear tool, such as the detectors 220, 222, 224, of nuclear tool 200, produces the measurement probe to evaluate the integrity of well material via the particular well material relationship maps. The following discussion applies to using the EM measurements with the nuclear measurements to determine the volumetric information of cement in a wellbore but a similar process can be used for other well materials in the wellbore.

To reduce the dependence on wellbore environment and enhance its sensitivity to a cement sheath, one example of operating a nuclear tool as disclosed herein and the signal processing of the nuclear measurements includes defining a signal S by taking the ratio of count rates from the relatively near detector ($N_{near}$) and the relatively far detector ($N_{far}$) from the nuclear tool as represented by Equation 1 presented below.

$$S = \frac{N_{near}}{N_{far}} \quad \text{Equation 1}$$

In example nuclear tool 200, there are two relatively far detectors, which provide different investigation depth into the radial distance of the wellbore 201. The longitudinal distance between the detector and the source and the energy level of photons emitted from the source can determine the radial depth of investigation (DOI). The analysis results from those two detectors serve as a quality control method to verify the confidence in well material evaluation. The processing method for the nuclear measurements is the same for both detectors. Therefore only the processing method from one set of near and far detector is discussed below but the method applies equally to the other set of near and far detector in the tool configuration. For example, in FIG. 2A, the relatively near detector is the first detector 220 and the relatively far detectors are the second detector 222 and the third detector 224.

The photon transport process inside materials can be computer simulated through the computational codes Monte Carlo N-Particle (MCNP) developed by Los Alamos National Lab. The process can be understood by looking at the attenuation law represented by Equation 2 below where N is the number of photons, μ is the linear attenuation coefficient, x is the distance traveled, and ρ is the material density.

$$N = N_0 \exp\left(-\sum_i \mu_i x_i \rho_i\right) \quad \text{Equation 2}$$

For a given well configuration with known tubing thickness and production casing thickness, the nuclear detector response due to the change of material inside the primary cement sheath can be simulated using MCNP codes. FIG. 6 presents an example of signal change (ΔS) when the cement annulus is fully filled with water, gas and barite mud compared to with intact cement (a baseline). As it shows, the signal change is proportional to the density contrast in the cement annulus. For a section of a wellbore with the same tubing thickness and production casing thickness of the simulation, the change in signal from the nuclear tool is indicative of the average density behind the casing. The curve of FIG. 6 represents a continuous function between a nuclear detector count rate variation and material density contrast. Four different measurement points that were used to fit the curve are also illustrated in FIG. 6.

This is further illustrated by an example of partitioned cement in the annulus, as shown in FIG. 7. FIG. 7 illustrates a nuclear tool signal contrast dependence on the volumetric fraction of cement inside a primary cement sheath. The cement annulus is partitioned into four quadrants as indicated by the three cement annulus examples 710, 720, and 730, in FIG. 7. These quadrants are replaced with water to create 75% filled with cement 710, 50% filled with cement 720, 25% filled with cement 710, and 0% filled with cement. For the 75% filled with cement 710, the water quadrant has four distinctive locations; for the 50% filled with cement 720, the water quadrants have two distinctive locations; for the 25% filled with cement 730, it mirrors that of the 75% filled with cement except that the water and cement are interchanged. FIG. 7 includes a line that plots the continuous function between nuclear detector count rate variation and material density contrast. Multiple measurement points are illustrated that were used to curve fit the line.

The signal change in each cement configuration compared to the full cement condition is illustrated in FIG. 7. As shown in FIG. 7, the signal change is proportional to the volumetric percentage of cement inside the cement annulus, which corresponds to an average density change. Thus if the change of signal is computed, the percentage of cement inside the cement annulus can be found through the relationship established between ΔS and $V_{cement}$ as represented by Equation 3 below.

$$V_{cement} = f(\Delta S) \quad \text{Equation 3}$$

The accuracy in estimating the cement volume can be deduced from FIG. 7 through error propagation. Different well material relationship maps can be developed via computer simulation for different well materials, such as a proppant, and used to determine the volumetric information. The particular type of well material can be known based on a given well-plan or from knowledge of the well operator.

Figure 8:
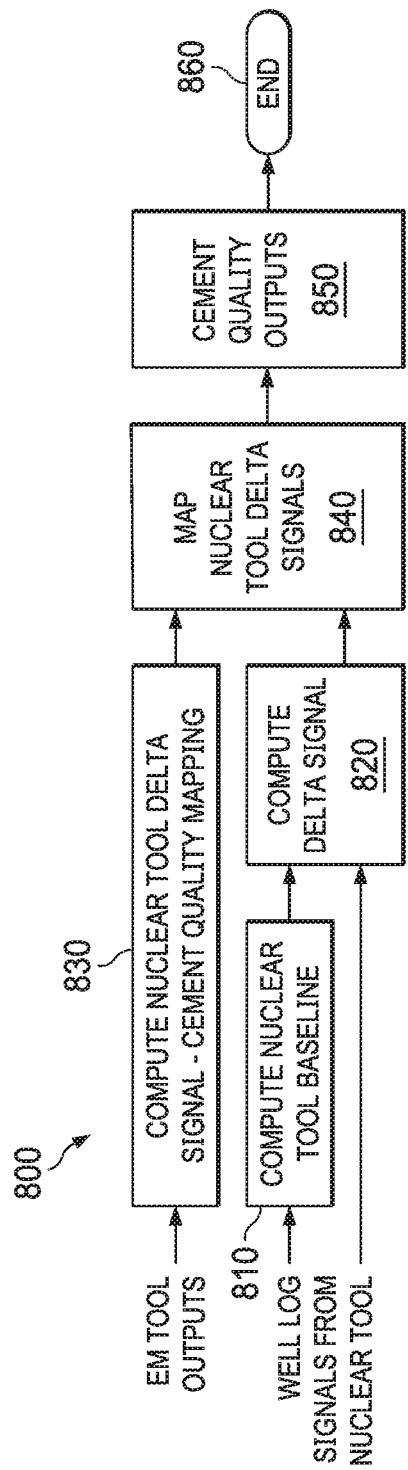
FIG. 8 illustrates an example workflow of a multi-physics algorithm to provide volumetric information of cement in a multi-pipe configuration.

FIG. 8 illustrates an example workflow 800 of a multi-physics algorithm to provide volumetric information of cement in a multi-pipe configuration. A similar process can also be used for other well materials. Inputs for the workflow 800 include a determined thickness of metal piping based on the measurements obtained from an EM tool (i.e., a piping properties from the EM measurements) and gamma ray measurements obtained from a nuclear tool (i.e., nuclear measurements). Workflow 500 provides an example of the determination of thickness of metal piping that can be used as an input for workflow 800. The EM tool and the nuclear tool can be, for example, the EM tool 152 and the nuclear tool 156. The EM tool and the nuclear tool can be integrated into a single well monitoring tool, such as the well integrity monitoring tool 150.

In a step 810, the workflow 800 determines a signal S baseline based on the nuclear measurements from the gamma ray detectors of the nuclear tool. The baseline can be calculated by taking the average of nuclear measurements over a depth range that is at least 2 feet, or using a peak of the histogram in the same depth range. The nuclear tool can be a NCET.

A delta of the signal S (ΔS) is determined in a step 820 based on the nuclear measurements of the gamma ray detectors. The delta of the signal S can be determined by subtracting the difference between the signal S baseline from step 810 and the signal S, the nuclear measurements from the nuclear tool. The delta of the signal S provides a processed nuclear measurement.

In a step 830 a delta of the signal S to well material integrity mapping is determined using the determined thickness of the metal piping. The nuclear measurement to cement integrity mapping can be performed using real measurements or computer simulations.

Figure 9:
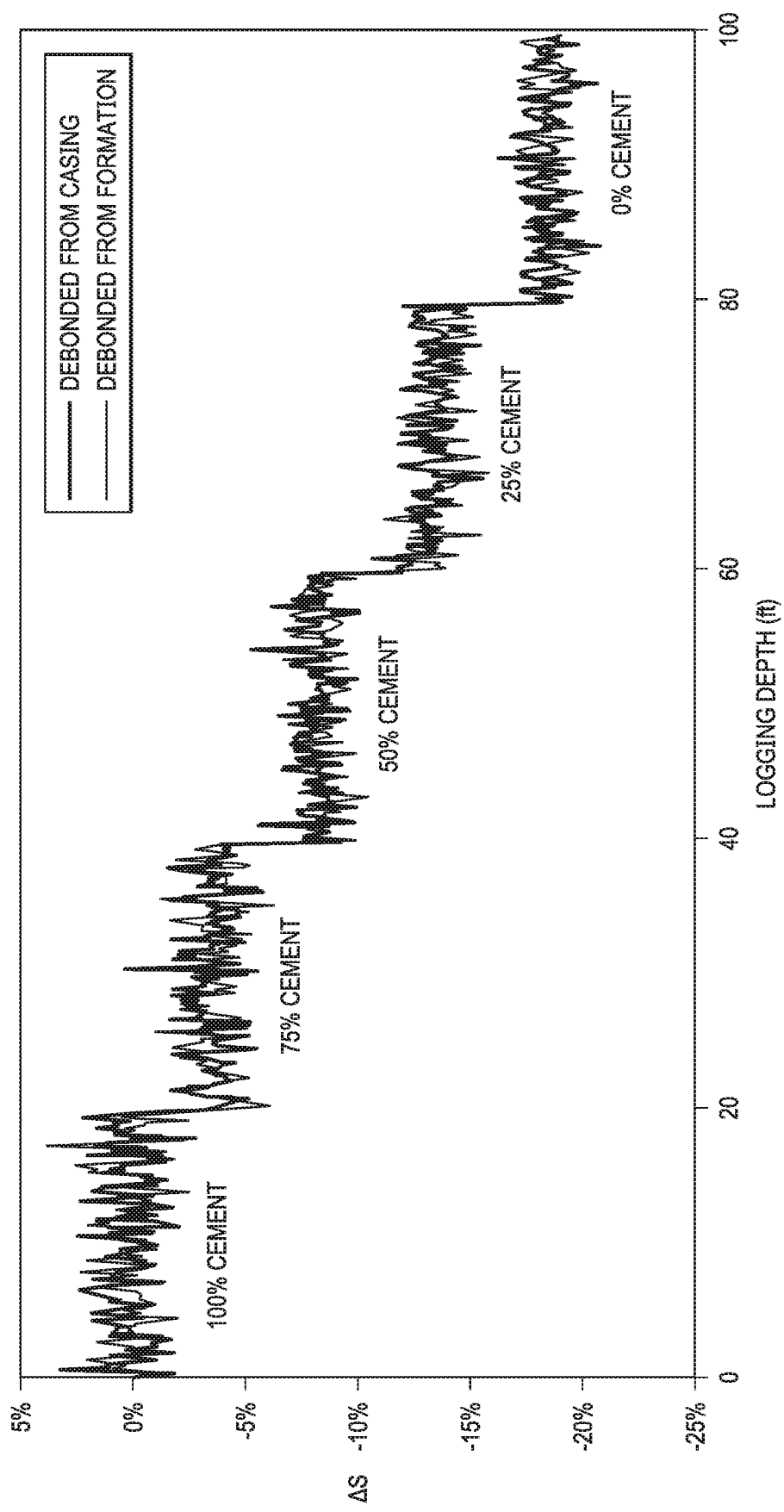
FIG. 9 illustrates a simulated log along an extended length of a wellbore with multiple cement conditions.

The well material relationship map to use is determined in a step 840. In one example, the well material relationship map is determined by employing both the delta signal of the nuclear tool measurements to well material quality mapping, such as represented in FIG. 6 or FIG. 7, and the delta of the signal S. The workflow 800 continues to step 850 where the integrity of well material is determined based on the relationship map, such as illustrated in FIG. 6 or FIG. 7. The functions represented by FIG. 6 and FIG. 7 provide examples of the nuclear part of the multi-physics algorithm that is used in step 850. FIG. 6 is for 100% material replacement in the annulus, water, cement, or other lighter or denser material. FIG. 7 is for water or cement in the annulus and replacing a volumetric fraction of cement with water at a time. FIG. 9 is an example of the results of step 850. The workflow 800 ends in a step 860.

FIG. 9 illustrates a simulated log along an extended length of a wellbore with multiple cement conditions. The nuclear tool can be run inside a production tubing and generate an extended log representing the cement volume behind the casing. Simulation results are provided in FIG. 9 from computer modeling. A well can be simulated with five distinctive sections of cement integrity. Each section runs for 20 feet including cement integrity scenarios such as 100% filled with cement, 75% filled with cement, 50% filled with cement, 25% filled with cement, and 0% filled with cement. The non-cement zone is filled with water instead.

The simulated log also considers the effect of debonding. Therefore, logs for two types of well integrity were generated. One type starts de-bonding from the casing side and the water zone propagate toward the formation side; the other typo starts de-bonding from the formation side and the water zone propagate toward the casing side.

The log results simulate a logging speed of 10 ft/min. Each data point represents a sum of measurements within 3 inch of depth. One observation from FIG. 9 is that 25% of cement packing difference is differentiable amid noise and uncertainty, which is consistent with the analysis from FIG. 7. A second observation is that the position of cement void inside the annulus is indistinguishable for the same amount of cement void.

Figure 10:
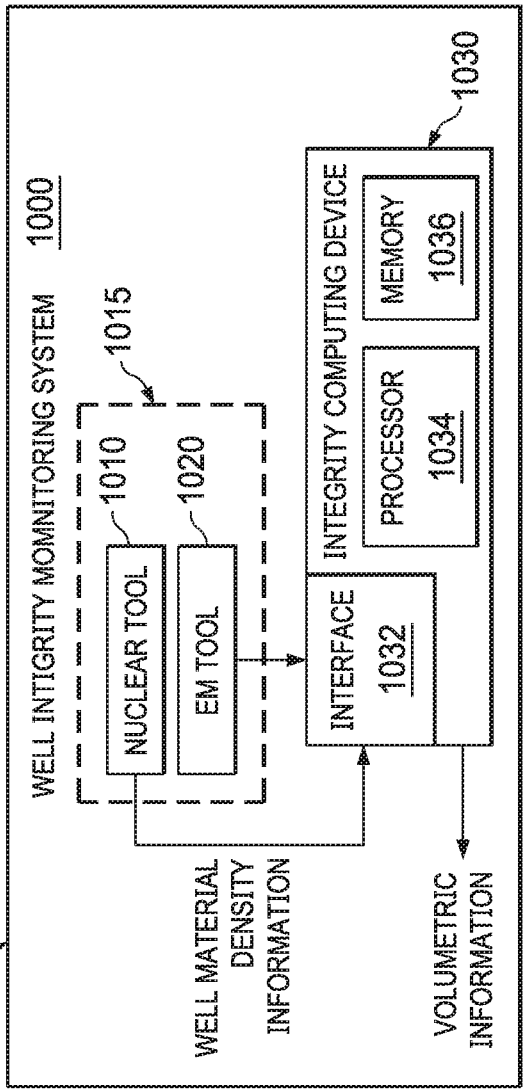
FIG. 10 illustrates a block diagram of an example of a well integrity monitoring system constructed according to the principles disclosed herein.

FIG. 10 illustrates a block diagram of an example of a well integrity monitoring system 1000 constructed according to the principles disclosed herein. The well integrity monitoring system 1000 includes a nuclear tool 1010 that obtains nuclear measurements from a wellbore having a casing configuration and an EM tool 1020 that obtains EM measurements of the metal piping of the casing configuration. An integrity computing device 1030 receives the nuclear measurements and EM measurements and determines a well material integrity, such as volumetric information of a well material within well annuluses defined by the metal piping. The components of the well integrity monitoring system 1000 can be communicatively coupled together via conventional connections and protocols used within the industry.

The well integrity monitoring system 1000, or at least some of the components thereof, can be integrated within a single body or enclosure. For example, the nuclear tool 1010 and the EM tool 1020 can be within a single enclosure 1015 such as represented by the dashed lines of FIG. 10. The integrity computing device 1030 can be located in an enclosure 1025 with the nuclear tool 1010 and EM tool 1020 or can be located at the surface of a wellbore. For example, the integrity computing device can be part of the electronic equipment 134. The integrity computing device 1030 can be programmed to perform the algorithms represented in the workflows of FIG. 5 and FIG. 8. The integrity computing device 1030 can also be configured to control the operations of the nuclear tool 1010 and the EM tool 1020. For example, the integrity computing device 1030 can be configured to coordinate the operations of the nuclear tool 1010 and the EM tool 1020 to obtain associated nuclear and EM measurements that correspond to a particular depth or depths of the wellbore.

The integrity computing device 1030 includes an interface 1032 configured to receive EM measurements and nuclear measurements obtained from a wellbore by a well integrity monitoring tool, such as disclosed herein. The nuclear and EM measurements can be signals from the nuclear tool 1010 and the EM tool 1020 that are processed before sending to the interface 1032. The EM measurements provide piping properties of the metal pipes in a wellbore. The nuclear measurements provide density information of the well material in the annuluses defined by the metal pipes. The integrity computing device also includes a processor 1034 configured to determine volumetric information of a well material within well annuluses defined by metal pipes of the casing configuration. The processor 1034 employs the EM and nuclear measurements to determine the volumetric information. The integrity computing device 1030 also includes a memory 1036. The memory 1036 can be a non-volatile memory that stores operating instructions to direct the operation of the processor 1034. The operating instructions can correspond to algorithms such as represented by the work flows of FIG. 5 and FIG. 8. The memory 1036 can also store various well material relationship maps that are employed to determine the volumetric information of the well material. The volumetric information provided by the integrity computing device can be provided to a user or well operator and used to make a well intervention decision.

Figure 11:
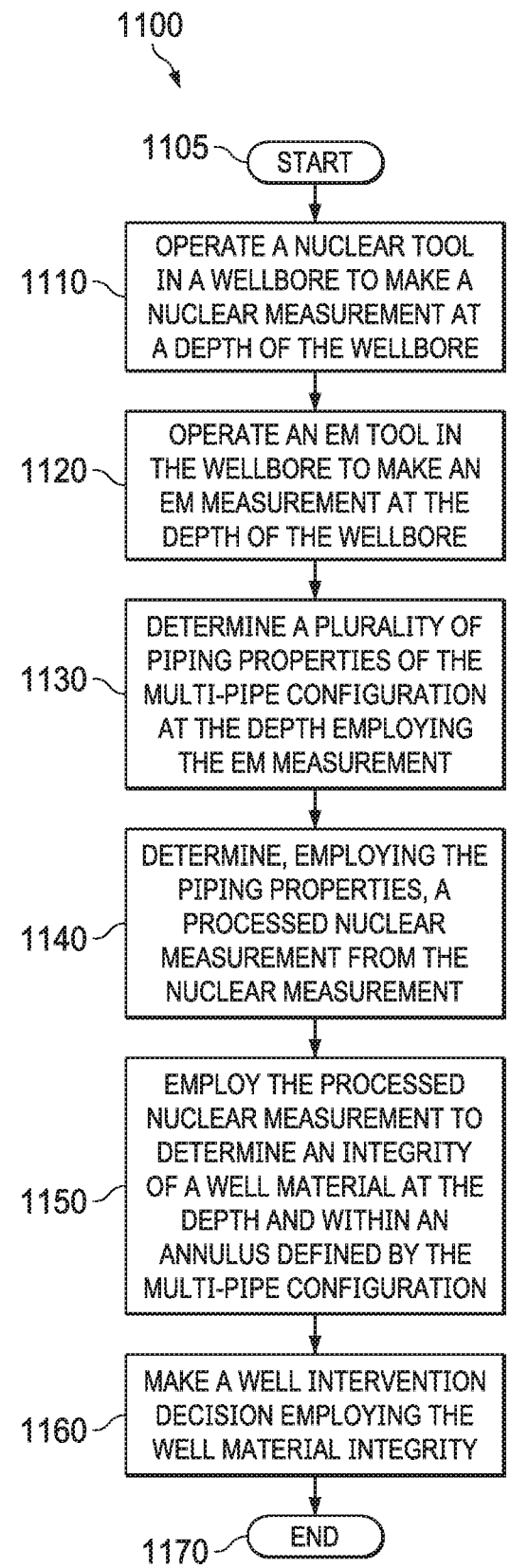
FIG. 11 illustrates a flow diagram of an example of a method of using a nuclear tool and an EM tool for well integrity monitoring of a wellbore having a multi-pipe configuration.

FIG. 11 illustrates a flow diagram of an example of a method 1100 of using a nuclear tool and an EM tool for well integrity monitoring of a wellbore having a multi-pipe configuration. The method 1100 advantageously combines the measurement outcomes from two types of tools of different physics principles and provides a more accurate downhole technique to assess the volumetric information of well materials behind multilayers of metal pipes in the multi-pipe configuration. Some of the steps of the method 1100 can be carried out, for example, by a processor of the electronic equipment 134 or the controller 160. Additionally, some of the steps of the method 1100 can be carried out by the integrity computing device 1030. The method 1100 begins in a step 1105.

In a step 1110, a nuclear tool is operated in a wellbore to make a nuclear measurement at a depth of the wellbore. The nuclear tool can be operated at multiple depths in the wellbore. The nuclear tool can be the nuclear tool 200 as disclosed herein.

The method 1100 continues by operating an EM tool in the wellbore to make an EM measurement at the depth of the wellbore. The EM tool can be operated at multiple depths in the wellbore that correspond to the operation of the nuclear tool. The EM tool can be the EM tool 300 or 400 as disclosed herein. In some examples, step 1120 can occur before or during step 1110.

In a step 1130, a plurality of piping properties of the multi-pipe configuration is determined at the depth employing the EM measurements. The piping properties can be determined by, for example, the workflow described in FIG. 5.

Employing the piping properties, a processed nuclear measurement is determined from the nuclear measurement in a step 1140. Processing of the nuclear measurement to determine the processed nuclear measurement can include computing a baseline for the nuclear measurements of the nuclear tool across a range of depths of the wellbore and subtracting the baseline from the nuclear measurement to produce the processed nuclear measurement.

In a step 1150, the processed nuclear measurement is employed to determine an integrity of a well material at the depth and within an annulus defined by the multi-pipe configuration. The processed nuclear measurement can be used with a well material relationship map to determine the well material integrity.

In a step 1160, a well intervention decision can be made employing the well material integrity. For example, an operator of a well can employ the well material integrity for well decommissioning. The method 1100 then ends in a step 1170.

This disclosure provides a method to evaluate cement integrity or other well material in multi-annuli for a well having a multi-pipe configuration. The disclosure combines the measurement outcomes from two types of tools of different physics principles and provides a mechanism to generate more accurate downhole technique to assess the volumetric information for cement or other well material behind multilayers of casing. The disclosed method, system and tool use EM measurement results and nuclear measurements, such as gamma radiation, to provide a better estimation of volumetric information about cement or other well material behind casing. The features of the disclosure can find application in a multi-string evaluation and provide an advantageous position in the emerging market of well decommissioning. The multi-physics approach improves the quality of measurement and increases the confidence in data output.

In one aspect, the disclosure provides a well integrity monitoring tool. In another aspect, the disclosure provides an integrity computing device. In yet another aspect, a system is also disclosed that includes the well integrity tool and the integrity computing device. The integrity computing device receives the nuclear and EM measurements and determines volumetric information of a well material within well annuluses defined by the metal piping.

Those skilled in the art to which this application relates will appreciate that other and further additions, deletions, substitutions and modifications may be made to the described embodiments.

The above-described apparatuses, systems or methods or at least a portion thereof may be embodied in or performed by various processors, such as digital data processors or computers, wherein the processors are programmed or store executable programs or sequences of software instructions to perform one or more of the steps of the methods or functions of the apparatuses or systems. The software instructions of such programs may represent algorithms and be encoded in machine-executable form on non-transitory digital data storage media, e.g., magnetic or optical disks, random-access memory (RAM), magnetic hard disks, flash memories, and/or read-only memory (ROM), to enable various types of digital data processors or computers to perform one, multiple or all of the steps of one or more of the above-described methods or functions of the system described herein.

Certain embodiments disclosed herein may further relate to computer storage products with a non-transitory computer-readable medium that have program code thereon for performing various computer-implemented operations that embody at least part of the apparatuses, the systems or carry out or direct at least some of the steps of the methods set forth herein. Non-transitory medium used herein refers to all computer-readable media except for transitory, propagating signals. Examples of non-transitory computer-readable medium include, but are not limited to: magnetic media such as hard disks, floppy disks, and magnetic tape; optical media such as CD-ROM disks; magneto-optical media such as floptical disks; and hardware devices that are specially configured to store and execute program code, such as ROM and RAM devices. Examples of program code include both machine code, such as produced by a compiler, and files containing higher level code that may be executed by the computer using an interpreter.

In interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, a limited number of the exemplary methods and materials are described herein. It is noted that as used herein and in the appended claims, the singular forms "a", "an", and "the" include plural referents unless the context clearly dictates otherwise.

Various aspects of the disclosure can be claimed including the apparatuses, systems, and methods disclosed herein. Aspects disclosed herein include:

A. A method, using a nuclear tool and an EM tool, for well integrity monitoring of a wellbore having a multi-pipe configuration, the method including: operating a nuclear tool in the wellbore to make a nuclear measurement at a depth of the wellbore, operating an EM tool in the wellbore to make an EM measurement at the depth of the wellbore, determining a plurality of piping properties of the multi-pipe configuration at the depth employing the EM measurement, determining, employing the piping properties, a processed nuclear measurement from the nuclear measurement, and employing the processed nuclear measurement to determine an integrity of a well material at the depth and within an annulus defined by the multi-pipe configuration.

B. A well integrity monitoring tool for a wellbore, including: an EM tool configured to obtain EM measurements, at different depths of a wellbore, associated with metal pipes of a multi-pipe configuration of the wellbore, wherein the EM measurements correspond to piping properties of the metal pipes, and a nuclear tool configured to obtain nuclear measurements at the different depths of the wellbore, wherein the nuclear measurements correspond to volumetric information for a well material that is behind a multilayer of the metal pipes.

C. A well integrity monitoring system, including: a well integrity monitoring tool for a wellbore having an EM tool configured to obtain EM measurements at depths of a wellbore having a multi-pipe configuration, wherein the EM measurements correspond to piping properties of metal pipes of the multi-pipe configuration, and a nuclear tool configured to obtain nuclear measurements at the depths of the wellbore, and including an integrity computing device having an interface configured to receive the EM measurements and the nuclear measurements, and a processor configured to employ both the EM measurements and the nuclear measurements to determine an integrity of a well material at one of the depths and within an annulus defined by the multi-pipe configuration.

Each of aspects A, B, and C can have one or more of the following additional elements in combination: Element 1: wherein the multi-pipe configuration includes a tubing and at least one string of casing. Element 2: wherein the determining the processed nuclear measurement includes computing a baseline for nuclear measurements of the nuclear tool at multiple depths of the wellbore. Element 3: wherein the determining the processed nuclear measurement further includes subtracting the baseline from the nuclear measurement to produce the processed nuclear measurement. Element 4: wherein the nuclear tool includes an omnidirectional gamma source, at least one gamma ray detector, and a barrier that is located between the omnidirectional gamma source and the at least one gamma ray detector. Element 5: wherein the nuclear tool has at least three gamma ray detectors. Element 6: wherein the EM tool is a frequency-domain or a time-domain tool. Element 7: wherein the plurality of piping properties include multiple ones of the properties selected from the list consisting of: tubing thickness, production casing thickness, distance between tubing and casing, distance between production casing and intermediate casing, and relative eccentricity between tubing and casing. Element 8: wherein at least one of the piping properties is calculated using an inversion process. Element 9: wherein the well material is selected from the list consisting of: cement, water, mud sediments, radioactive tag material, non-radioactive tag material, and proppants. Element 10: wherein the nuclear and EM tools are in a same tool string. Element 11: wherein the nuclear tool and the EM tool are collocated in a single body. Element 12: wherein the nuclear tool and the EM tool are collocated in a single body. Element 13: wherein the nuclear tool and the EM tool are in a same tool string. Element 14: wherein the nuclear tool includes an omnidirectional gamma source, at least one gamma ray detector, and a barrier that is located between the omnidirectional gamma source and the at least one gamma ray detector, and the EM tool is a frequency-domain or a time-domain tool. Element 15: wherein the nuclear tool has at least three gamma ray detectors. Element 16: wherein the EM measurements correspond to thickness and spacing information of at least some of the metal pipes of the multi-pipe configuration. Element 17: wherein the multi-pipe configuration includes a tubing and at least one string of casing. Element 18: wherein the well material integrity is volumetric information for the well material that is behind a multilayer of the metal pipes of the multi-pipe configuration. Element 19: wherein the processor is configured to determine the well material integrity by calculating the plurality of piping properties from the EM measurements, processing the nuclear measurements to produce a processed nuclear measurement employing the piping properties, and mapping the processed nuclear measurement to the well material integrity employing a well material relationship map. Element 20: wherein the processing includes computing a baseline from the nuclear measurements at multiple depths of the wellbore and subtracting the baseline from one of the nuclear measurements to produce the processed nuclear measurement. Element 21: wherein the processor is configured to determine at least one of the piping properties using an inversion process.

What is claimed is:

1. A method, using a nuclear tool and an electromagnetic (EM) tool, for well integrity monitoring of a wellbore having a multi-pipe configuration, the method comprising:
   operating the nuclear tool in the wellbore to make a nuclear measurement at a depth of the wellbore;
   operating the EM tool in the wellbore to make an EM measurement at the depth of the wellbore;
   determining a plurality of piping properties of the multi-pipe configuration at the depth employing the EM measurement;
   determining, by employing the piping properties, a representation of a relationship between EM measurements, nuclear measurements, and a well material for the multi-pipe configuration; and
   employing the EM measurement and the nuclear measurement with the representation to determine an integrity of the well material at the depth and within an annulus defined by the multi-pipe configuration, wherein the nuclear measurement is directed to density information of the well material and the EM measurement is directed to piping properties of the multi-pipe configuration.

2. The method as recited in claim 1 wherein the multi-pipe configuration includes a tubing and at least one string of casing.

3. The method as recited in claim 1 wherein the determining the relationship includes determining a processed nuclear measurement employing the piping properties by computing a baseline for nuclear measurements of the nuclear tool at multiple depths of the wellbore.

4. The method as recited in claim 3 wherein the determining the processed nuclear measurement further includes subtracting the baseline from the nuclear measurement to produce the processed nuclear measurement.

5. The method as recited in claim 1 wherein the plurality of piping properties include multiple ones of the properties selected from the list consisting of:
   tubing thickness,
   production casing thickness,
   distance between tubing and casing,
   distance between production casing and intermediate casing, and
   relative eccentricity between tubing and casing.

6. The method as recited in claim 1 wherein at least one of the piping properties is calculated using an inversion process.

7. The method as recited in claim 1 wherein the well material is selected from the list consisting of:
   cement,
   water,
   mud sediments,
   radioactive tag material,
   non-radioactive tag material, and
   proppants.

8. The method as recited in claim 1, wherein the nuclear tool includes an omnidirectional gamma source, at least one gamma ray detector, and a barrier that is located between the omnidirectional gamma source and the at least one gamma ray detector.

9. The method as recited in claim 8 wherein the nuclear tool has at least three gamma ray detectors.

10. The method as recited in claim 8 wherein the EM tool is a frequency domain or a time-domain tool.

11. The method as recited in claim 1, wherein the nuclear and EM tools are in a same tool string.

12. The method as recited in claim 1, wherein the nuclear tool and the EM tool are collocated in a single body.

13. A well integrity monitoring tool for a wellbore, comprising:
   an electromagnetic (EM) tool configured to obtain EM measurements, at different depths of a wellbore, associated with metal pipes of a multi-pipe configuration of the wellbore, wherein the EM measurements correspond to piping properties of the metal pipes; and
   a nuclear tool configured to obtain nuclear measurements at the different depths of the wellbore, wherein the nuclear measurements correspond to volumetric information for a well material that is behind a multilayer of the metal pipes, wherein an integrity of the well material at at least one of the different depths and within an annulus defined by the multi-pipe configuration is determined based on a representation, determined according to the piping properties, of a relationship between the EM measurements, the nuclear measurements, and the well material.

14. The well integrity monitoring tool as recited in claim 13 wherein the nuclear tool and the EM tool are collocated in a single body.

15. The well integrity monitoring tool as recited in claim 13 wherein the nuclear tool and the EM tool are in a same tool string.

16. The well integrity monitoring tool as recited in claim 13, wherein the nuclear tool includes an omnidirectional gamma source, at least one gamma ray detector, and a barrier that is located between the omnidirectional gamma source and the at least one gamma ray detector, and the EM tool is a frequency-domain or a time-domain tool.

17. The well integrity monitoring tool as recited in claim 16 wherein the nuclear tool has at least three gamma ray detectors.

18. The well integrity monitoring tool as recited in claim 13, wherein the EM measurements correspond to thickness and spacing information of at least some of the metal pipes of the multi-pipe configuration.

19. The well integrity monitoring tool as recited in claim 13, wherein the multi-pipe configuration includes a tubing and at least one string of casing.

20. The well integrity monitoring tool as recited in claim 13, wherein the well material is selected from the list consisting of:
cement,
water,
mud sediments,
radioactive tag material,
non-radioactive tag material, and
proppants.

21. A well integrity monitoring system, comprising:
a well integrity monitoring tool for a wellbore, including:
an electromagnetic (EM) EM tool configured to obtain EM measurements at depths of a wellbore having a multi-pipe configuration, wherein the EM measurements correspond to piping properties of metal pipes of the multi-pipe configuration, and
a nuclear tool configured to obtain nuclear measurements at the depths of the wellbore, and
an integrity computing device including:
an interface configured to receive the EM measurements and the nuclear measurements, and
a processor configured to employ both the EM measurements and the nuclear measurements to determine an integrity of a well material at one of the depths and within an annulus defined by the multi-pipe configuration based on a representation, determined according to the piping properties, of a relationship between the EM measurements, the nuclear measurements, and the well material, wherein the nuclear measurements are directed to density information of the well material.

22. The well integrity monitoring system as recited in claim 21 wherein the well material integrity is volumetric information for the well material that is behind a multilayer of the metal pipes of the multi-pipe configuration.

23. The well integrity monitoring system as recited in claim 22 wherein the representation is a well material relationship map between the EM measurements, a processed nuclear measurement, and the well material, wherein the processor is configured to calculate the piping properties from the EM measurements, process the nuclear measurements to produce a processed nuclear measurement by employing the piping properties, and map the processed nuclear measurement to the well material integrity employing the well material relationship map.

24. The well integrity monitoring system as recited in claim 23 wherein the processing includes computing a baseline from the nuclear measurements at multiple depths of the wellbore and subtracting the baseline from one of the nuclear measurements to produce the processed nuclear measurement.

25. The well integrity monitoring system as recited in claim 21, wherein the processor is configured to determine at least one of the piping properties using an inversion process.

* * * * *